United States Patent
Jing

(10) Patent No.: US 10,806,944 B2
(45) Date of Patent: Oct. 20, 2020

(54) LASER ACUPUNCTURE APPARATUS AND LASER ACUPUNCTURE DEVICE

(71) Applicants: BOE Technology Group Co., Ltd., Beijing (CN); HEFEI BOE Optoelectronics Technology Co., Ltd., Hefei, Anhui (CN)

(72) Inventor: Yangkun Jing, Beijing (CN)

(73) Assignees: BOE Technology Group Co., Ltd., Beijing (CN); HEFEI BOE Optoelectronics Technology Co., Ltd., Hefei, Anhui (CN)

(*) Notice: Subject to any disclaimer, the term of this patent is extended or adjusted under 35 U.S.C. 154(b) by 7 days.

(21) Appl. No.: 15/748,944

(22) PCT Filed: Sep. 21, 2017

(86) PCT No.: PCT/CN2017/102788
§ 371 (c)(1),
(2) Date: Jan. 30, 2018

(87) PCT Pub. No.: WO2018/153080
PCT Pub. Date: Aug. 30, 2018

(65) Prior Publication Data
US 2019/0366120 A1    Dec. 5, 2019

(30) Foreign Application Priority Data
Feb. 23, 2017   (CN) ........................ 2017 1 0099213

(51) Int. Cl.
*A61N 5/06* (2006.01)
*H04N 5/247* (2006.01)
(Continued)

(52) U.S. Cl.
CPC ........... *A61N 5/0619* (2013.01); *H04N 5/247* (2013.01); *A61N 2005/067* (2013.01);
(Continued)

(58) Field of Classification Search
CPC .......... A61N 5/06; A61H 39/00; A61B 5/021; A61B 5/024; A61B 5/053; A61B 5/08
(Continued)

(56) References Cited

U.S. PATENT DOCUMENTS

2018/0147416 A1* 5/2018 Segel .................. A61N 5/0619
2018/0280721 A1* 10/2018 Beckner .............. A61B 5/0816

FOREIGN PATENT DOCUMENTS

CN      202409857 U     9/2012
CN      205339523 U     6/2016
(Continued)

OTHER PUBLICATIONS

International Search Report issued in International Application No. PCT/CN2017/102788 dated Nov. 27, 2017 (8 pages).
(Continued)

*Primary Examiner* — Jon Eric C Morales
(74) *Attorney, Agent, or Firm* — Arent Fox LLP; Michael Fainberg

(57) ABSTRACT

This disclosure provides a laser acupuncture apparatus and a laser acupuncture device. The laser acupuncture apparatus includes: a bracket; an acupuncture unit movably installed on the bracket, where the acupuncture includes at least one laser emitter; an image capturer installed on the bracket; and a control unit coupled to the acupuncture unit and the image capturer, where the control unit is configured to analyze an image acquired by the image capturer, and to control the acupuncture unit according to an image analysis result to move relative to the bracket.

17 Claims, 2 Drawing Sheets

(51) Int. Cl.
*A61F 7/00* (2006.01)
*A61F 7/12* (2006.01)
*A61N 5/067* (2006.01)

(52) U.S. Cl.
CPC .............. *A61N 2005/0628* (2013.01); *A61N 2005/0659* (2013.01); *A61N 2005/0661* (2013.01); *A61N 2005/0663* (2013.01)

(58) Field of Classification Search
USPC .......................................................... 607/88
See application file for complete search history.

(56) References Cited

FOREIGN PATENT DOCUMENTS

| | | |
|---|---|---|
| CN | 105877999 A | 8/2016 |
| CN | 205626462 U | 10/2016 |
| CN | 106621070 A | 5/2017 |

OTHER PUBLICATIONS

Office Action issued in Chinese Application No. 201710099213.8 dated Feb. 8, 2018 (12 pages).
Office Action issued in Chinese Application No. 201710099213.8 dated Jul. 27, 2018 (8 pages).

* cited by examiner

LASER ACUPUNCTURE APPARATUS AND LASER ACUPUNCTURE DEVICE

This application is a US National Stage of International Application No. PCT/CN2017/102788, filed on Sep. 21, 2017, designating the United States, and claiming the priority to Chinese Patent Application No. 201710099213.8, filed with the Chinese Patent Office on Feb. 23, 2017 and entitled "A laser acupuncture system and a laser acupuncture device", which is hereby incorporated by reference in its entirety.

FIELD

This disclosure relates to the technical field of laser treatment devices, and particularly to a laser acupuncture system and a laser acupuncture device.

BACKGROUND

The laser acupuncture is a new acupuncture method by illuminating an acupoint using a very fine laser beam to treat a disease. Biological effects of laser generally include a thermal effect, a photo-piezo effect, a photochemical action, an electromagnetic effect, and a stimulation effect, and low-energy laser generally has anti-inflammatory effect, and can promote growth of epithelial cells, etc. As compared with the traditional acupuncture method, the laser acupuncture is characterized in that there is no pain arising from puncturing with a needle, there is no harm to a tissue, there is no needle being stuck or broken, there is no infection at a needle hole, and there are both a similar function of the traditional acupuncture, and a series of biological effects arising from laser per se.

All the laser acupuncture apparatuses in the related art are simple in function and structure, and a person needs to be assigned specially for operating and monitoring them during a treatment, so they have been less popularized and under-utilized.

SUMMARY

At least one embodiment of this disclosure provides a laser acupuncture apparatus including:
a bracket;
an acupuncture unit installed on the bracket, wherein the acupuncture unit is movable relative to the bracket, and the acupuncture includes at least one laser emitter;
an image capturer installed on the bracket; and
a control unit coupled to the acupuncture unit and the image capturer, where the control unit is configured to analyze an image acquired by the image capturer, and to control the acupuncture unit according to an image analysis result to move relative to the bracket.

In some embodiment of this disclosure, the acupuncture unit further includes: at least two laser emitters configured to emit laser of different wavelengths; and a condensing device configured to condense the laser beams emitted by the at least two laser emitters.

In some embodiment of this disclosure, the acupuncture unit includes two red laser emitters and one UV laser emitter; or the acupuncture unit includes two red laser emitters and one infrared laser emitter.

In some embodiment of this disclosure, the red laser emitters are helium-neon pulse laser emitters.

In some embodiment of this disclosure, the condensing device includes a triangular prism and a condensing lens, where three faces of the triangular prism are used respectively as incidence faces of beams from three laser emitters, and the condensing lens is located on an exiting light path of the triangular prism.

In some embodiment of this disclosure, the control unit is coupled to the condensing device and the at least one laser emitter, and configured to control and drive the condensing device to move, and to control and drive the at least one laser emitter to output laser.

In some embodiment of this disclosure, the image capturer includes two CCD image sensors arranged symmetric on two sides of the acupuncture unit to acquire images.

In some embodiment of this disclosure, the laser acupuncture apparatus further includes an infrared thermoscope installed on the bracket, where the infrared thermoscope is configured to sense temperature at a position where the laser of the acupuncture is acting.

In some embodiment of this disclosure, the control unit is coupled to the infrared thermoscope, and configured to adjust a laser output of the acupuncture unit according to a sensed signal of the infrared thermoscope.

At least one embodiment of this disclosure provides a laser acupuncture device including the laser acupuncture apparatus according to any one of the technical solutions above.

In some embodiment of this disclosure, the laser acupuncture device further includes a treatment bed; and the bracket of the laser acupuncture apparatus is movably installed on the treatment bed.

BRIEF DESCRIPTION OF THE DRAWINGS

In order to make the technical solutions in the embodiments of this disclosure more apparent, the drawings to be used in a description of the embodiments will be briefly introduced below, and apparently the drawings to be described below are merely illustrative of some embodiments of this disclosure, and those ordinarily skilled in the art can derive from these drawings other drawings without any inventive effort.

DETAILED DESCRIPTION OF THE EMBODIMENTS

In order to make the objects, the technical solutions and the advantages of this disclosure more apparent, the technical solutions according to the embodiments of this disclosure will be described below clearly and fully with reference to the drawings in the embodiments of this disclosure. Apparently the described embodiments are only a part but all of the embodiments of this disclosure. Based upon the embodiments of this disclosure here, all of other embodiments derived by those ordinarily skilled in the art without any inventive effort shall come into the scope of this disclosure as claimed.

Figure 1:
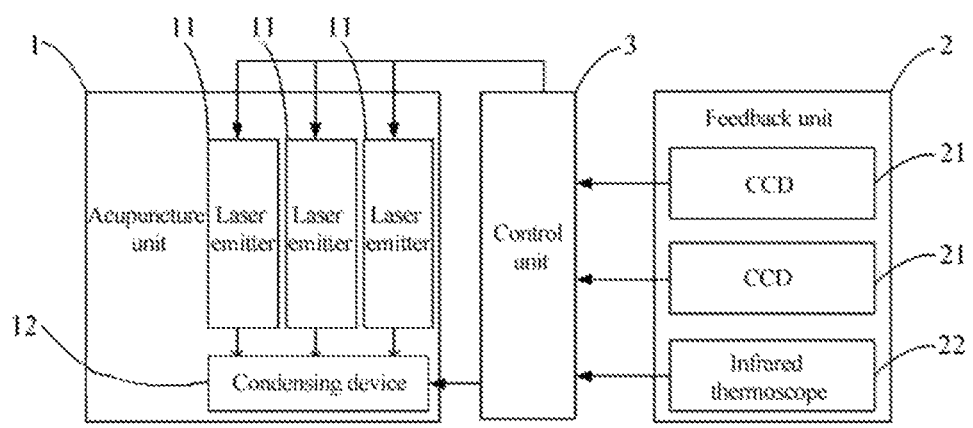
FIG. 1 is a structural block diagram of a laser acupuncture system according to an embodiment of this disclosure.
Figure 2:
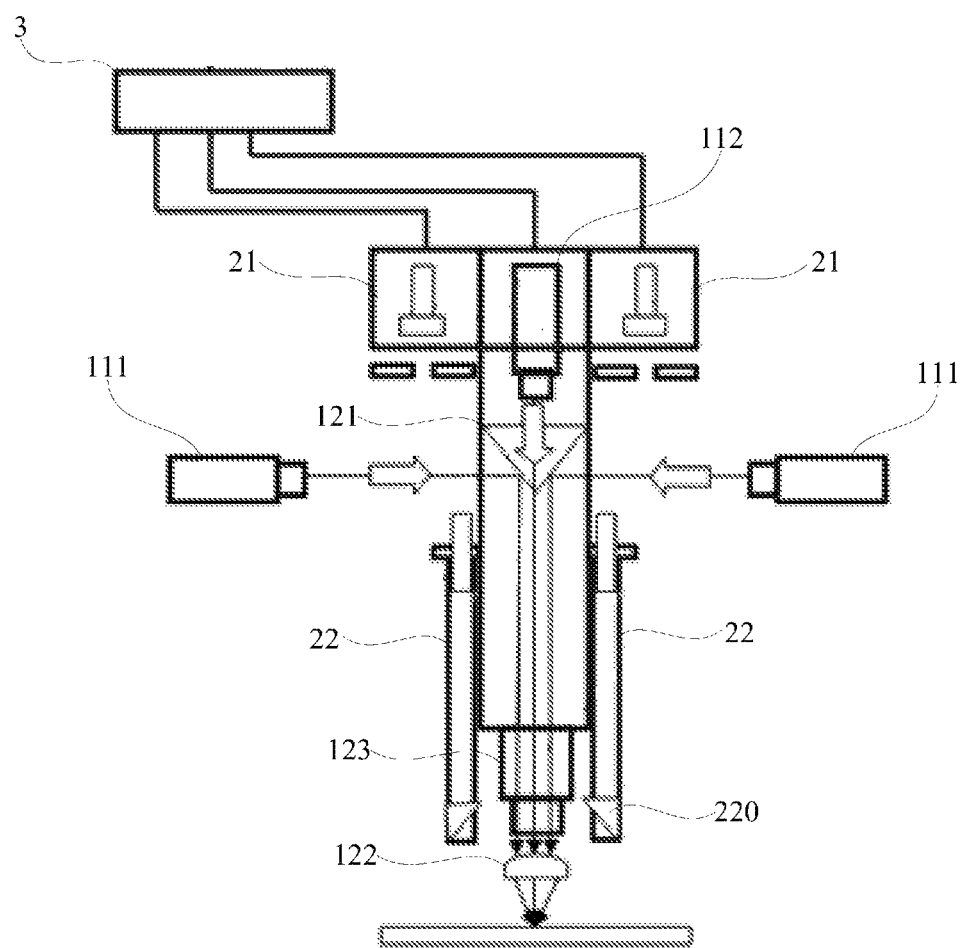
FIG. 2 is a schematic structural diagram of a laser acupuncture system according to an embodiment of this disclosure.

Reference will be made to FIG. 1 and FIG. 2.

As illustrated in FIG. 1 and FIG. 2, a laser acupuncture system according to an embodiment of this disclosure includes:
a bracket;

an acupuncture unit 1 installed on the bracket, where the acupuncture unit 1 can be moved relative to the bracket, and the acupuncture 1 includes at least one laser emitter 11;

a feedback unit 2 including an image capturer installed on the bracket, where the image capturer is configured to acquire an image of the body of a user; and a control unit 3 coupled to the acupuncture unit 1 and the image capturer, where the control unit is configured to analyze the image acquired by the image capturer, and to control the acupuncture unit 1 according to an image analysis result to move relative to the bracket.

In some embodiment, the control unit 3 may be implemented as a processor, or Central Processing Unit (CPU).

In some embodiment, the connection method of "being coupled to" may be referred to as two units or elements being connected in a wired or wireless mode, to thereby allow signal to be transmitted between the two units or elements.

In the laser acupuncture system above, information about an acupoint of the body of a patient, and particularly coordination information of the acupoint, for example, can be obtained using the image acquired by the image capturer, and program in the control unit 3; and the acupuncture unit 1 can be controlled automatically to move to thereby position a laser beam, so that there is a simple and convenient operating process for performing an acupuncture using the laser acupuncture system above, that is, it is simple and convenient to operate the laser acupuncture system above.

As illustrated in FIG. 1 and FIG. 2, in some embodiment, the acupuncture unit 1 can include at least two laser emitters 11, and a condensing device 12 configured to condense laser beams emitted by the at least two laser emitters 11, where there are different wavelengths of the laser beams emitted by the at least two laser emitters 11.

The laser beams at the different wavelengths run into the tissue of the human body till different depths, and also have different effects of acting on the tissue of the human body, so the laser emitters 11 at the different wavelengths can be enabled selectively to act on the human body for different treatment effects.

For example, the wavelength of laser emitted by a helium-neon (He—Ne) laser device is approximately 632.8 nm, the laser is red visible light, and after the biological tissue absorbs the laser in this band, such a photochemical action can be produced that directly activates enzyme. The laser in this band typically can run into the tissue until a depth ranging from 10 mm to 15 mm, so puncturing with a needle can be replaced therewith to stimulate the acupoint. But there is typically low power of the He—Ne laser device, so it is generally applied to moderate acupuncture simulation. There is a wide spectrum range and high power of a krypton (Kr) ion laser, so it can be applied to treat a disease needing strong simulation. The wavelength of laser emitted by a carbon dioxide ($CO_2$) laser device is approximately 10.6 μm, and the laser is far-infrared light which can be well absorbed by the biological tissue, where after the biological tissue absorbs the optical radiation at 10.6 μm, molecules of the tissue can be rotated (the entire molecule is rotated on some axis) and vibrated (relative shift between atomic nucleus without affecting their equilibrium positions), so that a chain of molecules is tensioned or bent, thus altering cytomembrane; and the far-infrared light can further promote activation and synthesis of the enzyme to thereby promote reproduction of the cells for the purpose of a healing. Since the far-infrared light has both thermal and simulation functions, and runs into the tissue till a small depth (approximately 0.21 mm), it generally acts on a shallow-layer skin, so it is typically applied to the laser acupuncture.

Further to the embodiment above, in some embodiment, the acupuncture unit 1 in the laser acupuncture system can include two red laser emitters and one UV laser emitter, or as illustrated in FIG. 2, the acupuncture unit 1 can include two red laser emitters 111 and one infrared laser emitter 112.

As illustrated in FIG. 2, furthermore the red laser emitters 111 can be helium-neon pulse laser emitters, where pulse laser acts on the acupoint of the human body as needle twirling in the traditional acupuncture, and thus can enable some specific therapy.

As illustrated in FIG. 2, further to the embodiment above, in some embodiment, the condensing device 12 in the therapy unit 1 can include one triangular prism 121 and one condensing lens 122, where three faces of the triangular prism 121 can be used respectively as light incidence faces of beams from three laser emitters 11, and beams of the three laser emitters 11 can be refracted in the triangular prism 121 to exit in parallel; and the condensing lens 122 can be located on an exiting light path on the light exit side of the triangular prism 121, and the parallel light exiting from the triangular prism 121 can be condensed by the condensing lens 122 to act on the acupoint of the human body. Of course, the condensing device 12 according to this embodiment can further include an optical lens 123, and other optical elements arranged between the triangular prism 121 and the condensing lens 122 to adjust an optical axis or a focal length.

As illustrated in FIG. 1 and FIG. 2, further to the respective embodiments above, in some embodiment, the control unit 3 in the laser acupuncture system can be coupled to the condensing device 12, and configured to control and drive the condensing device 12 to move; and the condensing device 12 can be controlled and driven to move to thereby vary the diameter of a spot, and the position of a focus, of the beam so as to adjust the area and the position of the acting laser.

Furthermore the control unit 3 can be further coupled to each laser emitter 11 to control and drive each laser emitter 11 to output laser.

As illustrated in FIG. 1 and FIG. 2, further to the respective embodiments above, in some embodiment, the image capturer in the feedback unit 2 of the laser acupuncture system can include two CCD image sensors 21, each of which is coupled to the control unit 3; and particularly the control unit 3 can include a PLC control circuit, a signal processing circuit, and other modules; the control unit 3 can store therein information about of body meridians map, and can analyze image information of the body of the user collected by the two CCD image sensors by matching it with the information about of the body meridians map, to thereby determine coordinate information of the acupoint of the user; and furthermore the control unit 3 can control the acupuncture unit to move, according to the coordinate information, so that the laser emitted by the acupuncture unit 1 is focused onto the acupoint of the body of the user.

As illustrated in FIG. 1 and FIG. 2, further to the respective embodiments above, in some embodiment, the feedback unit 2 in the laser acupuncture system can further include an infrared thermoscope 22 installed on the bracket, where the infrared thermoscope 22 is configured to sense temperature at a position where the laser beam of the acupuncture unit 1 is acting; and particularly an infrared receiver 220 of the infrared thermoscope 22 is oriented to the focal point where the laser beam of the acupuncture unit 1 is condensed.

As illustrated in FIG. 1 and FIG. 2, further to the embodiment above, furthermore the infrared thermoscope 22 can be coupled to the control unit 3; and the control unit 3 can adjust a laser output of the acupuncture unit 1 according to the temperature information sensed by the infrared thermoscope 22; and particularly the control unit 3 can control and adjust the power of a laser output of each laser emitter 11, and/or control each laser emitter 11 to be turned on or off, according to the temperature information fed back by the infrared thermoscope 22, to thereby perform acupuncture conditioning and treatment automatically according to a real-time condition, and can also avoid scalding and other accidents from occurring.

An embodiment of this disclosure further provides a laser acupuncture device including the laser acupuncture system according to any one of the embodiments above.

In some embodiment, the laser acupuncture device can further include a treatment bed, so that a user can be subjected to an acupuncture therapy while lying down thereon with his or her face downward.

As illustrated in FIG. 2, furthermore the bracket of the laser treatment system can be installed on the treatment bed, and can move relative to the treatment bed; and particularly the bracket of the laser treatment system can be driven by the control unit 3 to move horizontally and vertically relative to the treatment bed to thereby position the acupuncture unit 1.

Lastly it shall be noted that the foregoing embodiments are merely intended to illustrate the technical solutions according to this disclosure, but not to limit this disclosure thereto; and although this disclosure has been described in details with reference to the foregoing embodiments, those ordinarily skilled in the art shall appreciate that they still can modify the technical solutions recited in the foregoing respective embodiments, or make equivalent substitutions to a part of the technical features thereof, without departing from the spirit and scope of the technical solutions according to the respective embodiments of this disclosure.

The invention claimed is:

1. A laser acupuncture apparatus, comprising:
    a bracket;
    an acupuncture unit installed on the bracket, wherein the acupuncture unit is movable relative to the bracket, and comprises at least three laser emitters and a condensing device,
        wherein the condensing device is configured to condense laser beams emitted by the at least three laser emitters; the condensing device comprises a triangular prism, wherein three faces of the triangular prism are used respectively as incidence faces of beams from the three laser emitters;
    an image capturer installed on the bracket; and
    a control unit coupled to the acupuncture unit and the image capturer, wherein the control unit is configured to analyze an image acquired by the image capturer, and to control the acupuncture unit according to an image analysis result to move relative to the bracket.

2. The laser acupuncture apparatus according to claim 1, wherein
    at least two of the at least three laser emitters are configured to emit laser of different wavelengths.

3. The laser acupuncture apparatus according to claim 2, wherein the acupuncture unit comprises three laser emitters, wherein the three emitters comprise two red laser emitters and one non-red laser emitter.

4. The laser acupuncture apparatus according to claim 3, wherein the red laser emitters are helium-neon pulse laser emitters.

5. The laser acupuncture apparatus according to claim 3, wherein the condensing device further comprises a condensing lens, wherein the condensing lens is located on an exiting light path of the triangular prism.

6. The laser acupuncture apparatus according to claim 5, wherein the control unit is coupled to the condensing device and the at least three laser emitters, and configured to control and drive the condensing device to move, and to control and drive the at least three laser emitters to output laser.

7. The laser acupuncture apparatus according to claim 1, wherein the image capturer comprises two charge coupled device image sensors arranged symmetric on two sides of the acupuncture unit to acquire images.

8. The laser acupuncture apparatus according to claim 1, further comprises an infrared thermoscope installed on the bracket, wherein the infrared thermoscope is configured to sense temperature at a position where laser of the acupuncture is acting.

9. The laser acupuncture apparatus according to claim 8, wherein the control unit is coupled to the infrared thermoscope, and configured to adjust a laser output of the acupuncture unit according to a sensed signal of the infrared thermoscope.

10. A laser acupuncture device, comprising the laser acupuncture apparatus according to claim 1;
    wherein the laser acupuncture device further comprises a treatment bed; and
    the bracket of the laser acupuncture apparatus is movably installed on the treatment bed.

11. The laser acupuncture apparatus according to claim 2, further comprises an infrared thermoscope installed on the bracket, wherein the infrared thermoscope is configured to sense temperature at a position where laser of the acupuncture is acting.

12. The laser acupuncture apparatus according to claim 3, further comprises an infrared thermoscope installed on the bracket, wherein the infrared thermoscope is configured to sense temperature at a position where laser of the acupuncture is acting.

13. The laser acupuncture apparatus according to claim 4, further comprises an infrared thermoscope installed on the bracket, wherein the infrared thermoscope is configured to sense temperature at a position where laser of the acupuncture is acting.

14. The laser acupuncture apparatus according to claim 5, further comprises an infrared thermoscope installed on the bracket, wherein the infrared thermoscope is configured to sense temperature at a position where laser of the acupuncture is acting.

15. The laser acupuncture apparatus according to claim 6, further comprises an infrared thermoscope installed on the bracket, wherein the infrared thermoscope is configured to sense temperature at a position where laser of the acupuncture is acting.

16. The laser acupuncture apparatus according to claim 7, further comprises an infrared thermoscope installed on the bracket, wherein the infrared thermoscope is configured to sense temperature at a position where laser of the acupuncture is acting.

17. The laser acupuncture apparatus according to claim 3, wherein the non-red laser emitter is a UV laser emitter or an infrared laser emitter.

* * * * *